US00PP12125P2

(12) United States Plant Patent
Olesen et al.

(10) Patent No.: US PP12,125 P2
(45) Date of Patent: Oct. 9, 2001

(54) SHRUB ROSE PLANT NAMED 'POULWEETO'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/273,166

(22) Filed: Mar. 19, 1999

(51) Int. Cl.[7] ..... A01H 5/00
(52) U.S. Cl. ..... Plt./102
(58) Field of Search ..... Plt./102, 107, 141, Plt./148, 149

(56) References Cited

PUBLICATIONS

UPOV–ROM, 2000/04, Plant Variety Database, GTI Jouve Retrieval Software, 1 citation for 'Poulweet', 2 citations for 'Poulweeto'.*

* cited by examiner

*Primary Examiner*—Howard J. Locker

(57) ABSTRACT

A new garden rose plant which has abundant, pink flowers and attractive, disease resistant foliage, making this variety excellent for use in landscapes. This new and distinct variety has shown to be uniform and stable in the resulting generations from asexual propagation.

1 Drawing Sheet

SUMMARY OF THE INVENTION

The present invention consitutes a new and distinct variety of garden rose plant which originated from a controlled crossing between two unnamed seedlings. The two parents were crossed and the resulting seeds were planted in a controlled environment. The new variety is named 'POULweeto'.

The new rose may be distinguished from its seed parent, an unnamed seedling, by the following combination of characteristics:

1. The seed parent has blooms which are a paler pink than the blooms of 'POULweeto';

2. The seed parent has a lower growing and more spreading habit when compared to 'POULweeto'.

The new variety may variety may be distinguished from its pollen parent, an unnamed seedling, created by the same inventors, by the follow combination of characteristics:

1. The pollen parent is a patio rose, and is much smaller than 'POULweeto';

2. The pollen parent has orange-red blooms; whereas, 'POULweeto' has pink blooms;

3. The foliage of the pollen parent is much smaller than the foliage of 'POULweeto'.

The objective of the hybridization of this rose variety for garden use was to create a new and distinct variety with unique qualities, such as:

1. Uniform and abundant flowers combined with a long blooming season;

2. Vigorous, but compact growth;

3. Disease resistance;

4. Vigorous growth when propagated by cuttings.

This combination of qualities is not present in previously available commercial cultivars of this type and distinguishes 'POULweeto' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark. 'POULweet' was selected in the Spring of 1992 by the inventors as a single plant from the progeny of aforementioned hybridization.

Asexual reproduction of 'POULweeto' by cuttings and traditional budding was first done by L. Pernille and Mogens N. Olesen in their nursery in Fredensborg, Denmark in August 1993. This initial and other subsequent propagations conducted in controlled environments have demonstrated that the characteristics of 'POULweeto' are true to type and are transmitted from one generation to the next.

BRIEF DESCRIPTION OF THE DRAWINGS

The accompanying color illustration shows, as true as is reasonably possible to obtain in color photopraphs of this type, the typical characteristics of the buds, flowers, leaves, and stems, of 'POULweeto'. Specifically illustrated in SHEET 1:

1. Stem showing branching and the attachment of leaves, buds, and peduncles;

2. Flower bud, partially opened bud, and open bloom;

3. Flower petals, detached;

4. Sepals, and pedicel;

5. Flowering stem as well as a bare stem exhibiting thorns;

6. Leaves.

DETAILED DESCRIPTION OF THE VARIETY

The following is a description of 'POULweeto', as observed in its outdoor growth in a field nursery in Jackson County, Oreg. Observations were conducted during September, 1998. Color references are made using The Royal Horticultural Society (London, England) Colour Chart, 1995, except where common terms of color are used. For a comparison, several physical characteristics of the rose variety 'POULans', a rose variety from the same inventors described and illustrated in U.S. Plant Pat. No. 9,664 and issued on Oct. 22, 1996 are compared to 'POULweeto'in Chart 1.

CHART 1

| | 'POULweeto' | 'POULans' |
|---|---|---|
| Size of open bloom. | 35–45 mm. | 45–55 mm. |
| Petalage. | Semi-double, 10–15 petals. | Double, 18–26 petals. |
| Bud form. | Short, pointed ovoid. | Round with flat top. |

Parents:
*Seed parent.*—Unnamed seedling.
*Pollen parent.*—Unnamed seedling.
Classification:
*Botanical.*—*Rosa hybrida.*
*Commercial.*—Shrub.

FLOWER AND FLOWER BUD

Blooming habit: Continuous.
Flower bud:
*Size.*—Upon opening, 20 mm in length from base of receptacle to end of bud.
*Bud form.*—Short, pointed ovoid.
*Bud color.*—As sepals unfold, Red Group 52B. Red Group 55A at ¼ opening.
*Sepals.*—Green Group 143A. Moderate foliaceous appendages on three sepals. Commonly produces a sixth sepal, located inside of regular sepals. The sixth sepal is normally reduced in size and lacks foliaceous appendages. Surfaces of sepals Moderately pubescent. Stipitate glands are very limited and primarily located on foliaceous appendages.
*Receptacle.*—Surface: Smooth. Shape: Urn-shaped. Size: Large for the size of the flower. 8 mm (h)×7 mm (w). Color: Yellow-Green Group 144B.
*Pedicel.*—Surface: Long stipitate hairs in moderate numbers. Length: 40 mm to 45 mm. Average length. Color: Yellow-Green Group 144A. Strength: Upright to pendulant.
*Borne.*—2–7 buds per flowering stem.
Flower bloom:
*Fragrance.*—Light fruity fragrance. Stipitate glands on pedicels have strong fragrance of clove when touched.
*Duration.*—As a cut flower 3 to 5 days. The blooms have a duration on the plant of approximately 4 to 6 days. Petals fall cleanly away from plant.
*Size.*—Small, average flower diameter is 35–45 mm when open.
*Form.*—Shallow cup.
*Shape of flower when viewed from the side.*—Upon opening, upper part: Flat. Upon opening, lower part: Flat. Open flower, upper part: Flat. Open flower, lower part: Flattened convex.
*Petalage.*—Semi-double, Average range: 10–15 petals under normal conditions with 0–3 petaloids.
Color:
*Upon opening, petals.*—Outermost petals: Upper Surface: Red Group 55C. Reverse Side: Red Group 55B. Innermost petals: Upper Surface: Red-Purple Group 65B. Reverse Side: Red-Purple Group 58D.
*Upon opening, basal petal spots.*—Outer Side: Green-Yellow Group 1C. Inner Side: Green-Yellow Group 1C.
*After opening, petals.*—Outermost petals: Upper Surface: Red Group 55D. Reverse Side: Red Group 55B. Innermost petals: Upper Surface: Red-Purple Group 65B. Reverse Side: Red-Purple Group 62C.
*After opening, basal petal spots.*— Green-Yellow Group 1B to Green-White Group 157C.
General tonality: On open flower Red Group 55C. No change in the general tonality at the end of the 3rd day. Afterwards, general tonality is Red Group 56A, due in large part by a change in color of margin of petal to Red Group 56C creating a blend of colors.
Petals:
*Petal reflex.*—Innermost petals cupped inwards, outer most petals flat to slightly reflexed.
*Petal edge.*—Ruffled.
*Shape.*—Round to deltoid shaped
*Petaloids.*—Few present. Quantity: 0–3.
*Thickness.*—Average to thin.
*Arrangement.*—Informal.
Reproductive organs:
*Pollen.*—Color: Yellow Group 14B. Quantity: Average.
*Anthers.*—Size: Small. Color: Immature, Yellow-Green Group 152D, maturing to Grey-Brown 199B. Quantity: Average. Filaments: Color: Green-White Group 157A. Stigmas: Position: Typically at same height as the anthers. Color: Yellow-Green Group 145D.
*Styles.*—Color: Yellow-Green Group 145D. Immediately below stigma the style can exhibit slight intonation of Red-Purple Group 57D.
Hips: None observed

PLANT

Plant growth: Vigorous, but even growth somewhat spreading. When grown as a budded field grown plant on *Rosa multiflora* understock the average height of the plant itself is 80 cm and the average width is 75 cm.
Stems:
*Color.*—Young wood: Yellow-Green Group 144C–144D. Older wood: Yellow-Green Group 144C.
*Thorns.*—Incidence: Moderate. Size: Average length: 8 mm. Color: Yellow-Green Group 145B–145A. Shape: Deeply concave to concave to curved downward.
*Surface.*—Young wood: Smooth. Older wood: Smooth.
Plant foliage: Normal number of leaflets on leaves in middle of the stem: 5–7 leaflets.
*Leaf size.*—Medium, with individual leaflet size being small. 90–95 mm (1)×60–70 mm (w).
*Quantity.*—Above average.
*Color.*—Upper Leaf Surface: Green Group 137B. Lower Leaf Surface: Green Group 138B–138C. Juvenile foliage: Upper leaf surface: Green Group 138B with moderate intonations of Greyed-Red Group 180A on margins. Lower leaf surface: Green Group 138B with moderate intonations of Greyed-Red Group 180A on margins and undersurface. Anthocyanin: Location: Upper & lower leaflet surfaces, rachis, petioles, stem and thorns. Color: Greyed-Red Group 180A.
Plant leaves and leaflets:
*Stipules.*—Size: 12 mm–14 mm. Color: Green Group 137C. Stipitate glands: Located on the margins.
*Petiole.*—Length: 15 mm–20 mm. Color: Green Group 137C. Underneath: Smooth, lacks prickles, with moderate to above average numbers of stipitate glands.

*Rachis.*—Color: Green Group 137C. Underneath: Smooth, lacks prickles. Upper Margins: With moderate to above average numbers of stipitate glands.

*Leaflet.*—Edge: Finely serrated. Shape: Ovate. Texture: Matte, thick to leathery.

Disease resistance: Above average resistance to mildew, black spot, and Botrytis under normal growing conditions in Jackson County, Oreg.

Cold hardiness: POULweeto has been found to be cold hardy in Fredensborg, Denmark and in Jackson County, Oreg.

We claim:

1. A new and distinct variety of rose plant of the shrub class, substantially as herein illustrated and described as a distinct and novel rose variety due to its abundant, pink flowers, vigorous but even growth, disease resistance, and extended period of bloom.

* * * * *

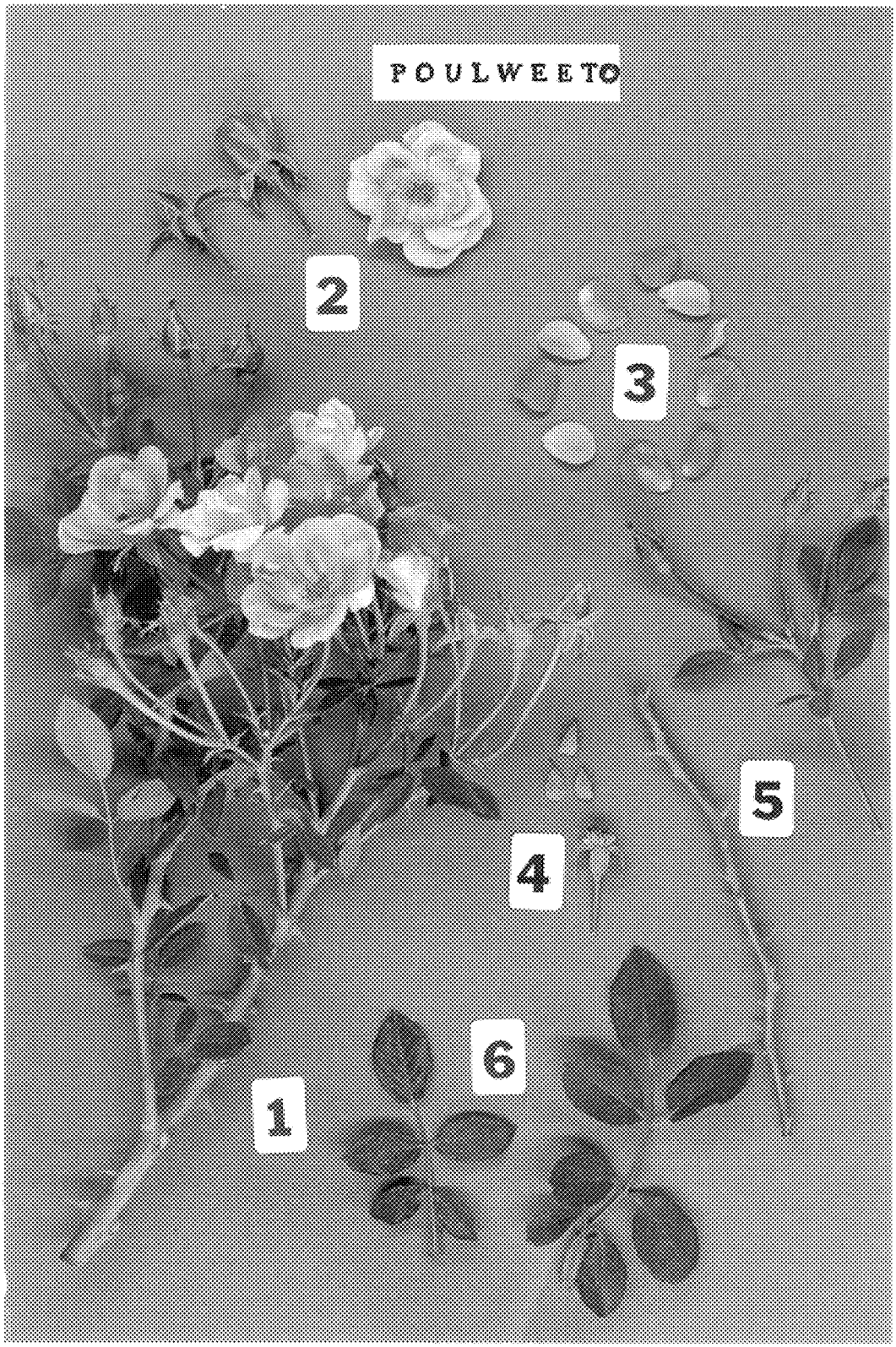
POULWEETO
2
3
5
4
6
1